(12) United States Patent
Marchant et al.

(10) Patent No.: US 10,159,229 B2
(45) Date of Patent: Dec. 25, 2018

(54) CONTINUOUS PRODUCTION SYSTEM FOR CULTURING DIPTERAN INSECTS

(71) Applicant: Enterra Feed Corporation, Langley (CA)

(72) Inventors: Brad Marchant, Vancouver (CA); Andrew Vickerson, Vancouver (CA); Oliver Kaulfuss, New Westminster (CA); Reed Radley, Vancouver (CA)

(73) Assignee: Enterra Feed Corporation, Langley, British (CA)

( * ) Notice: Subject to any disclaimer, the term of this patent is extended or adjusted under 35 U.S.C. 154(b) by 86 days.

(21) Appl. No.: 15/327,955

(22) PCT Filed: Jul. 13, 2015

(86) PCT No.: PCT/CA2015/050653
§ 371 (c)(1),
(2) Date: Jan. 20, 2017

(87) PCT Pub. No.: WO2016/011541
PCT Pub. Date: Jan. 28, 2016

(65) Prior Publication Data
US 2017/0202191 A1     Jul. 20, 2017

Related U.S. Application Data

(60) Provisional application No. 62/027,081, filed on Jul. 21, 2014.

(51) Int. Cl.
*A01K 67/033*   (2006.01)
*F21V 7/22*     (2018.01)
*F21Y 113/00*   (2016.01)

(52) U.S. Cl.
CPC ...... *A01K 67/033* (2013.01); *A01K 2227/706* (2013.01); *F21V 7/22* (2013.01); *F21Y 2113/00* (2013.01)

(58) Field of Classification Search
CPC .............................. A01K 67/033; A01K 29/00
(Continued)

(56) References Cited

U.S. PATENT DOCUMENTS 2,670,562 A * 3/1954 Gould .................... A01K 97/04
                                                            119/6.5
3,939,883 A   2/1976 Harrell
(Continued)

FOREIGN PATENT DOCUMENTS

CA        2834412       11/2012
CN     201185612 Y      1/2009
(Continued)

OTHER PUBLICATIONS

Biopod: the future offood waste diversion and recycling, Black Soldier Fly Forum: Breeding BSF in captivity, Reply #22 "Re: not easy" by earthtiger, Nov. 26, 2011 (Nov. 26, 2011), URL: httQ:/lthebioQod.co111/folUmlindex.QhQ?toQic=175.15.
(Continued)

*Primary Examiner* — Yvonne R Abbott-Lewis
(74) *Attorney, Agent, or Firm* — Casmir Jones S.C.; J. Mitchell Jones (57) ABSTRACT

Methods and apparatus are provided for culturing Dipteran insects, particularly *Hermetia illucens*. The apparatus include a mating chamber that contains adult insects, and adaptations for the scheduled and/or metered introduction of inputs, such as: empty egg laying substrate, prepupae, bedding, carbohydrate (sugar) and/or water); and, the scheduled and/or metered collection of outputs, such as: egg laying substrate containing eggs, exuvia and bedding, and/or dead adults. The systems may also include adaptations to optimize the use of space, including the use of controlled environmental conditions within a confined space.

16 Claims, 7 Drawing Sheets

(58) Field of Classification Search
USPC .................................................. 119/6.6, 6.5
See application file for complete search history.

(56) References Cited

U.S. PATENT DOCUMENTS

| | | | | |
|---|---|---|---|---|
| 4,334,498 | A * | 6/1982 | Bedding | A01K 67/033 119/6.7 |
| 4,368,690 | A * | 1/1983 | Tenzer | A01K 67/033 119/496 |
| 4,411,220 | A * | 10/1983 | Voegele | A01K 67/033 119/6.6 |
| 4,417,545 | A * | 11/1983 | Finney | A01K 67/033 119/6.6 |
| 4,765,274 | A * | 8/1988 | Pizzol | A01K 67/033 119/6.6 |
| 4,765,275 | A * | 8/1988 | Yukawa | A01K 67/033 119/6.5 |
| 4,850,305 | A | 7/1989 | Georgi | |
| 5,042,427 | A * | 8/1991 | Bedding | A01N 63/00 119/6.7 |
| 5,158,497 | A | 10/1992 | Rossignol | |
| 5,351,643 | A * | 10/1994 | Hughes | A01K 67/033 119/6.5 |
| 5,759,224 | A | 6/1998 | Olivier | |
| 5,819,685 | A * | 10/1998 | Kappelt | A01K 67/033 119/6.5 |
| 6,244,213 | B1 * | 6/2001 | Tedders | A01K 67/033 119/6.6 |
| 6,391,620 | B1 | 5/2002 | Olivier | |
| 6,397,782 | B1 | 6/2002 | Cope | |
| 6,557,487 | B1 | 5/2003 | Fleischmann | |
| 6,780,637 | B2 | 8/2004 | Olivier | |
| 6,786,001 | B1 | 9/2004 | Piper | |
| 6,863,022 | B2 * | 3/2005 | Fleischmann | A61K 35/63 119/6.5 |
| 6,938,574 | B2 | 9/2005 | Zhang | |
| 8,322,305 | B2 | 12/2012 | Chang | |
| 9,462,795 | B2 * | 10/2016 | Chin | A01K 67/033 |
| 9,510,572 | B2 * | 12/2016 | Aldana | A01K 67/033 |
| 9,844,223 | B2 | 12/2017 | Vickerson et al. | |
| 2002/0177219 | A1 | 11/2002 | Olivier | |
| 2003/0143728 | A1 | 7/2003 | Olivier | |
| 2003/0233982 | A1 | 12/2003 | Zhang | |
| 2008/0163541 | A1 | 7/2008 | Harris | |
| 2011/0081452 | A1 | 4/2011 | Hem et al. | |
| 2011/0174222 | A1 | 7/2011 | Lee | |
| 2011/0296756 | A1 | 12/2011 | Zhang | |
| 2012/0187041 | A1 | 7/2012 | Popa | |
| 2014/0020630 | A1 * | 1/2014 | Courtright | A01K 29/00 119/6.6 |
| 2016/0219887 | A1 * | 8/2016 | Vickerson | A01N 63/02 |

FOREIGN PATENT DOCUMENTS

| | | |
|---|---|---|
| CN | 102329155 A | 1/2012 |
| CN | 101889629 B | 9/2012 |
| WO | 00/69791 | 11/2000 |
| WO | 2010/002188 | 1/2010 |
| WO | 2012/100077 | 7/2012 |
| WO | 2013/166590 | 11/2013 |

OTHER PUBLICATIONS

Bradley, S. W. and Sheppard, D. C. 1984. House Fly Oviposition Inhibition by Larvae of Hermetia illucens, the Black Soldier Fly. Journal of Chemical Ecology, 19, 853-859.

Enterra Feed Corporation. Enterra Natural Fertilizer™ Product Specifications. Jul. 2014 (Jul. 2014) and Jlme 2013 (Jun. 2013) [online PDF document, retrieved on Oct. 2, 2014 (Feb. 10, 2014)]. Retrieved from the internet: <URL: http://enterrafeed.coml wp-contentiuploadsIN atural-Fertilizer. pdf>.

Enterra Feed Corporation. CTVNews—"Bugs Life"—Enterra Feed Corporation. Nov. 4, 2013 (Nov. 4, 2013) [online video, retrieved on Oct. 2, 2014 (Oct. 2, 2014)]. Retrieved from the internet: <URL: http://www.enterrafeed.comlctv-news-bugs-lifevideo/> or from: <URL: http://www.youtube.comlwatch?v=VBHVg_tdTLM>.

Erickson, M. C., M. Islam, C. Sheppard, J. Liao, and M. P. Doyle. 2004. Reduction of *Eschericia coli* 0157:H7 and *Salmonella enterica* serovar Enteritidis in chicken manure by larvae of the black soldier fly. J. Food Protection. 67: 685-690.

Foster, S.P. et al. Behavioral manipUlation methods for insect pest-management. Annual Review a/Entomology, 1997, vol. 42, pp. 123-146, ISSN: 0066-4170 (Print).

Furman, D. P., R. D. Young, and E. P. Catts. 1959. Hermetia illucens (Linnaeus) as a factor in the natural control of *Musca domestica* Linnaeus. J. Econ. Entomol. 52: 917-921.

Green, T.R. et al. Applied Biochemistry and Biotechnology, online Jan. 12, 2012 (Jan. 12, 2012), Mar. 2012 (Mar. 2012), vol. 166, No. 6, pp. 1381-1387.

Hogsette, J. A. 1985. New diets for production of house flies and stable flies (Diptera: Muscidae) in the laboratory. J. Econ. Entomol. 85: 2291-2294.

Larde, Investigation on Some Factors Affecting Larval Growth in a Coffee-Pulp Bed, Biological Wastes 30 (1989) 11-19.

Larde, Recycling of Coffee Pulp by Hermetia illucens (Diptera: Stratiomyidae) Larvae, Biological Wastes 333 (1990) 307-310.

Liu, Q., Tomerblin, J. K., Brady, J. A., Sanford, M. R., and Yu, Z. 2008. Black Soldier Fly (Diptera: Stratiomyidae) Larvae Reduce *Escherichia coli* in Dairy Manure. Environ. Entomol. 37(6): 1525-1530.

Myers, et al., Development of Black Solder Fly (Diptera: Stratiomyidae) Larvae Fed Dairy Manure, Environ. Entomol. 37(1): 11-15(2008).

Newton, et al. Using the Black Soldier Fly, *Hermetia illucens*, as a Value-Added Tool for the Management of Swine Manure, Jun. 6, 2005, pp. 1-17, https://www.cals.ncsu.edu/waste_mgt/smithfield_projects/phase2report05/cd,web%20files/A2.pdf.

Olivier, P.A. (2009) "Utilizing lower life forms for the bioconversion of putrescent waste." Black Soldier Fly Blog—Official Website., pp. 1-4.

Sheppard et al, A Value Added Manure Management System Using the Black Soldier Fly, Bioresource Technology 50 (1994) 275-279.

Sheppard, D.C J.K.; J.K. Tomberlin, J.A. Joyce, B.C. Kiser & S.M. Sumner. 2002. Rearing Methods for the Black Soldier Fly (Diptera: Stratiomyidae). J. Med. Entomol. 39(4): 695-698.

Sheppard et al, Black Soldier Fly Prepupae a Compelling Alternative to Fish Meal and Fish Oil, a Public Comment Prepared in Response to a Request by the National Marine isheries Service Nov. 15, 2007, pp. 1-5, http://www.aquacircle.org/images/pdfdokumenter/udvikling/andre/amerika/Soldier_fly_compelling_alternative_NOAA-USDA.pdf.

St-Hilaire et al, Fly Prepupae as Feedstuff for Rainbow Trout, Journal of the World Aquaculture Society, vol. 38, No. 1, Mar. 2007, pp. 59-67.

St-Hilaire et al, Fish Offal Recycling by the Black Soldier Fly Produces a Foodstuff High in Omega-3 Fatty Acids, Journal of the World Aquaculture Society, vol. 38, No. 2, Jun. 2007, pp. 309-313.

Temple, W.D. et al. Use of Enterra Natural Fertilizer (Black Soldier Fly Larvae 1-20 Digestate) as a Soil Amendment. Enterra Feed Corporation, Nov. 2013 (Nov. 2013) [online PDF document, retrieved on Oct. 2, 2014 (Oct. 2, 2014)]. Rctrieved from the Internet: <URL: http://www.certifiedorgank.bc.ca/programs/osdpll-l72]rass_Research_Final%20Report.pdf>.

Tomberlin & Sheppard, Lekking Behavior of the Black Soldier Fly (Diptera: Stratiomyidae) Florida Entomologist, 84 (4) Dec. 2001, 729-730.

Tomberlin, J.K. & D.C. Sheppard. 2002. Factors Influencing Mating and Oviposition of Black Soldier Flies (Diptera: Stratiomyidae) in a Colony. J. Entomol. Sci. 37(4): 345-352.

Tomberlin, J.K., D. C. Sheppard & J.A. Joyce. 2002. Selected Life-History Traits of Black Soldier Flies (Diptera: Stratiomyidae) Reared on Three Artificial Diets. Ann. Entomol. Soc. Am. 95(3): 379-386.

Tomberlin, J. K., Alder, P. H., and Myers H. M. 2009. Development of the Black Soldier Fly (Diptera: Stratiomyidae) in Relation to Temperature. Environ. Entomol.38: 930-934.

(56) References Cited

OTHER PUBLICATIONS

Tossell, I. Conversation with David Suzuki leads to maggot-based animal feed. The Globe and Mail, Oct. 28, 2013 (Oct. 28, 2013) [online newspaper article, retrieved on Oct. 2, 2014 (Oct. 2, 2014)]. Retrieved from the internet: <URL: http://www.theglobeandmail. comlreport-on-business/small-business/starting-out! conversation-with-david-suzuki-leads-to-maggot-based-animal-feedlarticlel5114182/>.
Zhang, et al. 2010. An artificial light source influences mating and oviposition of black soldier flies, *Hermetia illucens*. J. Insect Sci.10:1-7.
Beetles—Coleoptera—Overview. (n.d.). Retrieved Apr. 2017, from http://eol.org/pages/345/overview.
Scarabaeidae. (Jul. 5, 2017). Retrieved Apr. 2017, from https://en.wikipedia.org/wiki/Scarabaeidae.
ISR & Written Opinion from PCT/CA2013/000457 dated Aug. 2, 2013.
ISR & Written Opinion from PCT/CA2014/050727 dated Oct. 22, 2014.
ISR & Written Opinion from PCT/CA2015/050653 dated Sep. 29, 2015.
EESR from European Patent Application No. 13787121.6 dated Oct. 30, 2015.
Restriction Requirement from U.S. Appl. No. 14/397,679 dated Mar. 7, 2016.
Office Action from U.S. Appl. No. 14/397,679 dated May 13, 2016.
Office Action from European Application No. 13787121.6 dated Jun. 27, 2016.
Office Action from U.S. Appl. No. 14/908,924 dated Apr. 27, 2017.
EP Search Report, EP Patent Application No. 15824967.2, dated Dec. 18, 2017.

\* cited by examiner

CONTINUOUS PRODUCTION SYSTEM FOR CULTURING DIPTERAN INSECTS

FIELD OF THE INVENTION

Aspects of the invention relate to systems and conditions adapted to enclose and continuously culture insects through various stages of an insect life cycle, particularly flying insects that lay eggs to produce larvae. Mechanized systems are provided that are adapted for the large scale production of insect larvae, which may be used in linked bioconversion systems, for example systems designed to convert organic waste materials into valuable outputs.

BACKGROUND OF THE INVENTION

Some insect larvae, such as the larvae of the black soldier fly (BSF; *Hermetia illucens*) are particularly well suited to converting a wide variety of organic materials into alternative products. The organic material may for example include commercial or residential waste products, such as fruit and vegetable matter, coffee pulp, meat, fish, bread, grains, or manures. The value-added products of BSF bioconversion may for example, include livestock feed or feed ingredients (for terrestrial or aquatic animals), pet food, food stuffs for human consumption, or plant growth media. To take advantage of this natural aptitude for bioconversion, various techniques for utilizing BSFs in bioconversion systems have been described, see: WO2013166590, WO2012100077 and WO2010002188, There are a number of characteristics of BSFs that have been considered advantageous in alternative bioconversion systems. BSF larvae and prepupae are high in protein and fatty acid content and exhibit natural behaviors that can form the basis of self-harvesting systems. BSF adults are not generally considered to be disease vectors. BSF larvae may demonstrate anti-pathogenic qualities (Erickson, et al. 2004; Liu, et al. 2008). Finally, BSF larvae may be cultured so as to produce stable colonies, at least in part because they deter colonization from other insect species (Bradley and Sheppard, 1984) and can survive in a variety of environmental conditions.

As a member of the Family Stratiomyidae, the BSF goes through full metamorphosis during its lifespan. This includes the egg, larval, pupae and adult life cycle stages. Larvae will hatch from the egg stage after 48-72 hours and go through five instars (larval stages) before reaching the pupae stage. The first instar (L1) will molt into the second instar (L2) within 4-5 days and generally reach the pupae stage within a further 12-30 days, depending on temperature, humidity, type of feed, quantity of feed, frequency of feeding, mixture of feed ingredients, moisture of feed, starter diet, finishing diet and consistency of feed. Between the fifth instar (L5) and the pupae stage is the prepupae stage, where BSF larvae generally seek a drier environment to complete the metamorphosis stage of its life cycle. The pupae stage generally lasts 7-20 days, depending on factors such as, for example, movement, proximity to other moving pupae, level of light, temperature and humidity, following which the adult fly will emerge. Adult BSFs mate and gravid female BSFs will lay eggs (i.e., "oviposit") for the next generation. The life span of an adult BSF is generally 6-15 days, depending on humidity (e.g., 50-90%) and/or temperature (e.g., 22-35° C.) and stored energy, such as quantities and profiles of protein and fat. The foregoing timelines associated with the typical BSF life cycle are necessarily approximations, with variations that generally depend on environmental conditions and food supply. For example, it has been reported that limited food supply can extend the larval period to 4 months (Furman et al., 1959).

Under appropriate conditions, gravid female BSF adults will oviposit eggs approximately 24-72 hours after mating. Eggs are generally oviposited in tight, narrow spaces, such as blocks of cardboard with flutes oriented in any direction. Females are typically attracted to oviposition sites with pungent odours, or other biochemical signals derived from BSF eggs or gravid BSF females, as this usually indicates a potential food source for BSF offspring. BSF adults require specific environmental conditions to induce mating behaviors, including particular ranges of light, space, temperature and humidity. BSF will survive and mate at temperatures between 22° C. and 35° C. and humidity levels between 30% and 90%. For example, BSF will survive and mate at an ambient air temperature of approximately 25° C.-30° C. with a relative humidity of approximately 60-80%. It has been reported that a BSF colony can be maintained at 22° C. (Tomberlin and Sheppard, 2002) and that the upper limit for optimal development of the BSF is between 30-36° C. (Tomberlin et al., 2009). A study measuring BSF mating and oviposition reported that 80% percent of egg clutches were deposited when humidity exceeded 60% (Tomberlin and Sheppard, 2002).

SUMMARY

Aspects of the invention relate to apparatus and methods for culturing Dipteran insects, particularly *Hermetia illucens*. In selected aspects, the invention includes a mating chamber that contains adult insects. The mating chamber may include adaptations for the scheduled and/or metered introduction of inputs, such as: empty egg laying substrate, prepupae, bedding, carbohydrate (sugar) and/or water); and, the scheduled and/or metered collection of outputs, such as: egg laying substrate containing eggs, exuvia and bedding, and/or dead adults. The system may also include adaptations to optimize the use of space, including the use of controlled environmental conditions within a confined space.

In selected embodiments, the invention includes a mating chamber and a bioconversion unit, which work in concert to facilitate alternating stages of the insect life cycle. The mating chamber is adapted to house male and female adult insects that mate to produce insect eggs. The eggs may then be transferred from the mating chamber to the bioconversion unit for rearing, where insect larvae are cultured to produce matured larvae. The mature larvae may in turn be transferred to the mating chamber, to eclose to produce a subsequent generation of egg-laying adult insects.

In selected embodiments, the mating chamber is an enclosure, such as a screened enclosure, for containing the adult insects, adapted to permit air circulation into and out of the enclosure and to admit external illumination into the enclosure. The enclosure may be provided with an entry port and an exit port for oviposition chambers, which may take the form of egg-laying trays stocked with an egg-laying substrate and suitable oviposition media. Similarly, the enclosure may also be provided with an separate entry port and an exit port for a prepupae chamber.

An oviposition chamber support housed within the enclosure may be adapted to convey an egg laying substrate in the oviposition chamber from the oviposition chamber entry port to the oviposition chamber exit port. Similarly, a prepupae chamber support housed within the enclosure, adapted to convey the prepupae chamber from the prepupae chamber entry port to the prepupae chamber exit port. A mort collection system may be disposed along the base of the mating chamber, adapted to convey dead insects out of the mating chamber through a mort exit port in the enclosure.

A mechanism may be provided for sequentially passing oviposition chambers through the enclosure along the oviposition chamber support during a metered ovipositioning period. Similarly, a mechanism may be provided for sequentially passing prepupae chambers through the screened enclosure along the prepupae chamber support during a metered prepupae maturation period. In general, the prepupae maturation period will be longer than the ovipositioning period.

The bioconversion unit may include a plurality of segregated larval compartments each adapted to house insect larvae and growth media. The bioconversion unit may further include a mechanism for sequentially feeding metered growth media to the larvae in a selected larval compartment.

Eggs produced in the mating chamber on the egg-laying substrate may be seeded in a neonate larval compartment of the bioconversion unit, for example by transferring the egg-laying substrate to the neonate larval compartment and providing a neonate food source in the neonate larval compartment accessible to neonate insect larvae. An approximated collection of eggs may be seeded in the neonate compartment, allowed to hatch and to migrate away from the egg-laying substrate, to mature on the neonate food source to produce matured neonate larvae, leaving barren egg laying substrates. Barren egg-laying substrates may then be sequentially separated from matured neonate larvae and neonate larval compartments, and returned to oviposition chambers in the mating chamber, and matured neonate larvae are then sequentially fed with metered growth media in larval compartments of the bioconversion unit, to produce matured larvae. Metered populations of matured larvae may then be sequentially transferred to the prepupae chambers in the mating chamber to eclose to produce the adult insects.

The mating chamber and bioconversion unit may be housed in a climate-controlled enclosure, such as a greenhouse, that admits sunlight, and the mating chamber may be positioned within the climate-controlled enclosure so that sunlight reaches the adult insects within the mating chamber.

DETAILED DESCRIPTION

Various embodiments of the invention provide apparatus and methods for producing and isolating BSF eggs in a self-contained environment, including the inducement of mating and the isolation and collection of eggs with minimal disruption of adult fly behavior.

The Figures illustrate various aspects of a system for producing and isolating BSF eggs. The apparatus includes mating chamber 10 and artificial light source(s) 12 a mort (dead fly) collector 14, an oviposition chamber 16 and oviposition chamber support 18. An attractant for gravid females may be provided in oviposition chamber 16. Prepupae chambers 20 ride on prepupae chamber support 22. Feed containers may be provided to convey adult insect food, such as granulated sugar, along the oviposition chamber support or the prepupae chamber support, and the feed containers may for example take the form of prepupae chambers that are stocked with the insect food rather than being seeded with matured larvae.

Mating chamber 10 may for example be constructed of a frame 24 and mesh 26 structure, which may for example stand alone, as illustrated, or hang from an overhead support. In the illustrated embodiment, the top portion 28 of mating chamber 10 is rectangular in transverse cross section, with a v-shaped bottom portion 30. The length, width and height of the cage are variable, and repeating units may for example be provided that are attachable to form a modular structure of alternative dimensions. For general context, an example of one workable dimension would be approximately 60 ft long, 5 ft wide and 10 ft high. Mating chamber 10 may be placed on casters or rails to facilitate movement of the chambers for servicing or cleaning. In this way, the system may for example be adapted to allow mating chambers 10 to be placed side-by-side, thereby reducing space between adjacent mating chambers 10 and reducing the overall footprint of the facility.

Artificial lights (bulbs and fixture) may be placed so as to illuminate the interior space of mating chambers 10, for example being positioned above the mating chamber. For example, a combination of LED, quartz iodine, or halogen neodymium bulbs may be used. A high UV spectrum light (black light) can also be used, for example to attract flies to certain areas of the cage to increase lekking behavior or for luring flies to or away from particular areas, for example to minimize escapees during repair or servicing of the system.

The bottom portion 30 of mating chamber 10 may be trough shaped, as illustrated, for example with an angle of less than about 40 degrees. The trough shape may be adapted to direct dead flies (morts) into the lowest portion of the trough, which may in turn be fashioned into a tubular mort collection system 14 adapted to convey morts out of the mating chamber. For example, inside the bottom portion of trough 30, a rotatable screw conveyor or auger may be positioned so that when the screw is rotated it directs dead flies to one end of mating chamber 10, and out through a mort exit port. For dimensional context, the mort collection system may for example be made from a tubular structure that is approximatly 2.5" in diameter. In selected embodiments, a vacuum may for example be attached to the tube at the mort exit port, temporarily or permanently, to aid in the collection of morts. In a mort collection system such as this, the screw feeder may for example be turned mechanically, for example with a manual crank shaft or with an electric motor. The mort collection system may be operated so as to facilitate frequent and thorough removal of dead flies, so as to prevent the spread of pathogens, such as mite infestations, and prevent gravid females from being attracted to decomposing dead flies.

The mating chamber may be operated as a modular conveyor of prepupae and oviposition chambers, on a sequential first in, first out, in-line accumulating conveyor basis. In such a system, the addition of a freshly stocked prepupae chamber at one end of the mating chamber, through an entry port, may be carried out so as to cause the oldest prepupae chamber to exit at the other end of the mating chamber through an exit port. Similarly, the addition of a freshly stocked oviposition chamber at one end of the mating chamber, through an oviposition chamber entry port, may be carried out so as to cause the oldest oviposition chamber to exit at the other end of the mating chamber, through the oviposition chamber exit port.

Figure 1:
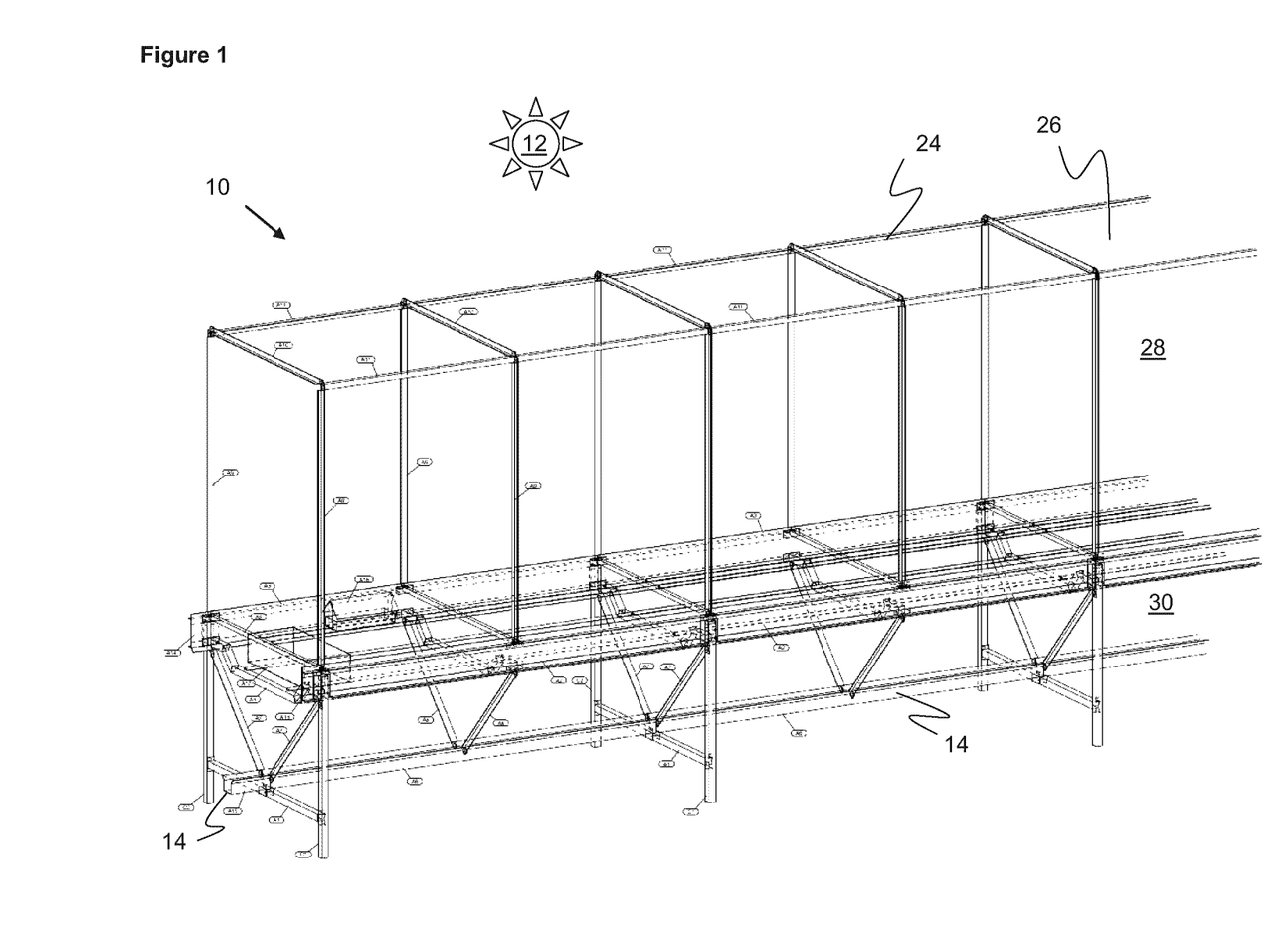
FIG. 1 is an isometric view of a selected embodiment of a mating chamber, illustrating a screened enclosure adapted to house male and female insects under conditions adapted to facilitate mating to produce harvestable eggs.
Figure 2:
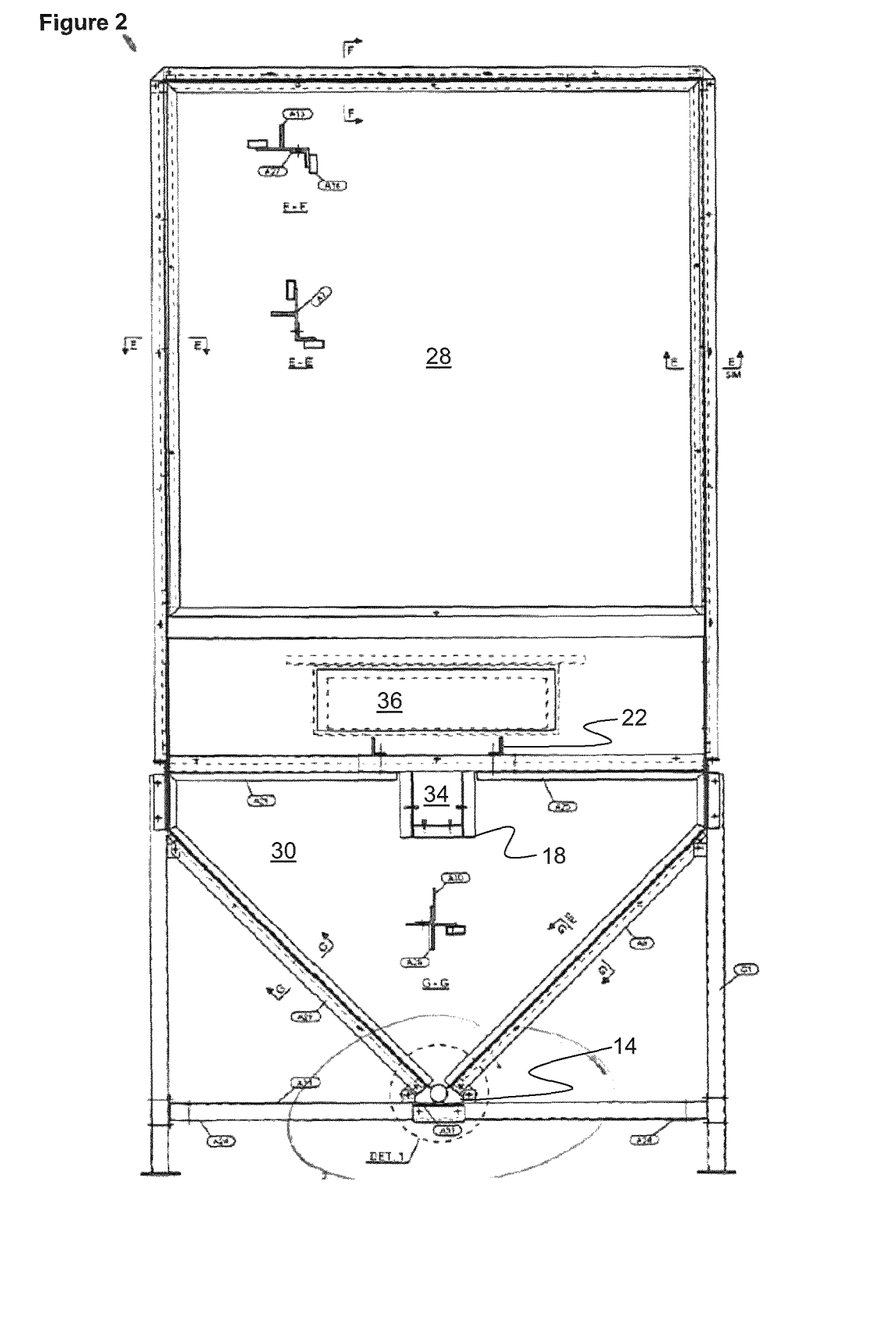
FIG. 2 is end elevation view of the mating chamber, illustrating a port for a prepupae chamber, above a port for an oviposition chamber, which in turn is above a mort exit port in the enclosure.
Figure 3:
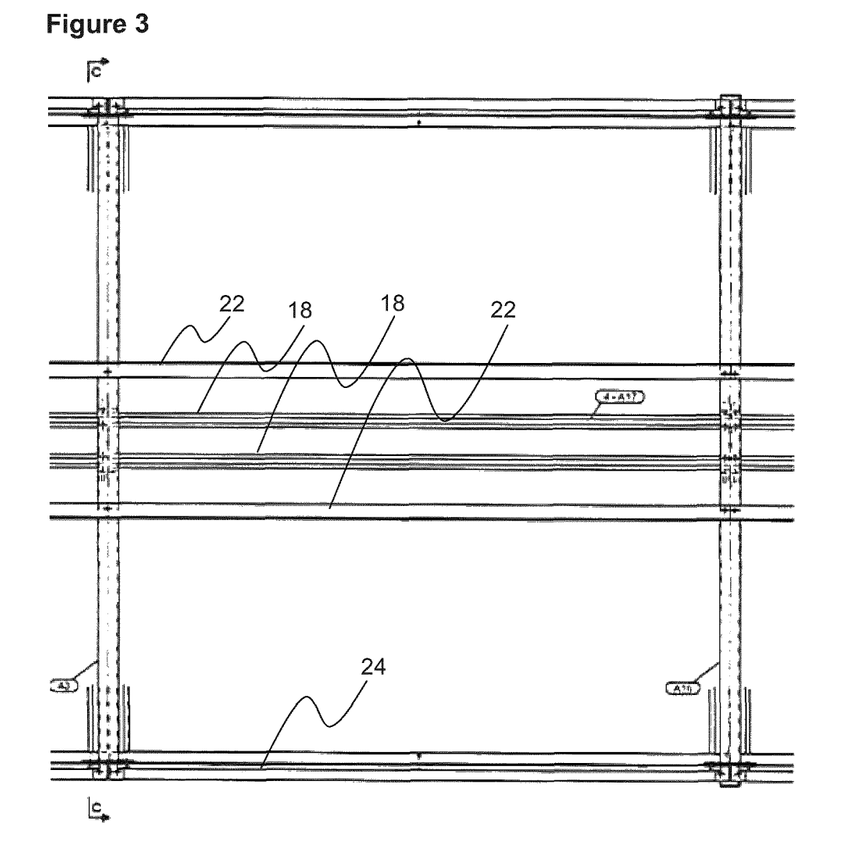
FIG. 3 is a top view of the mating chamber, illustrating oviposition chamber support rails and prepupae chamber support rails, within the framework at the base of the screened enclosure.
Figure 4:
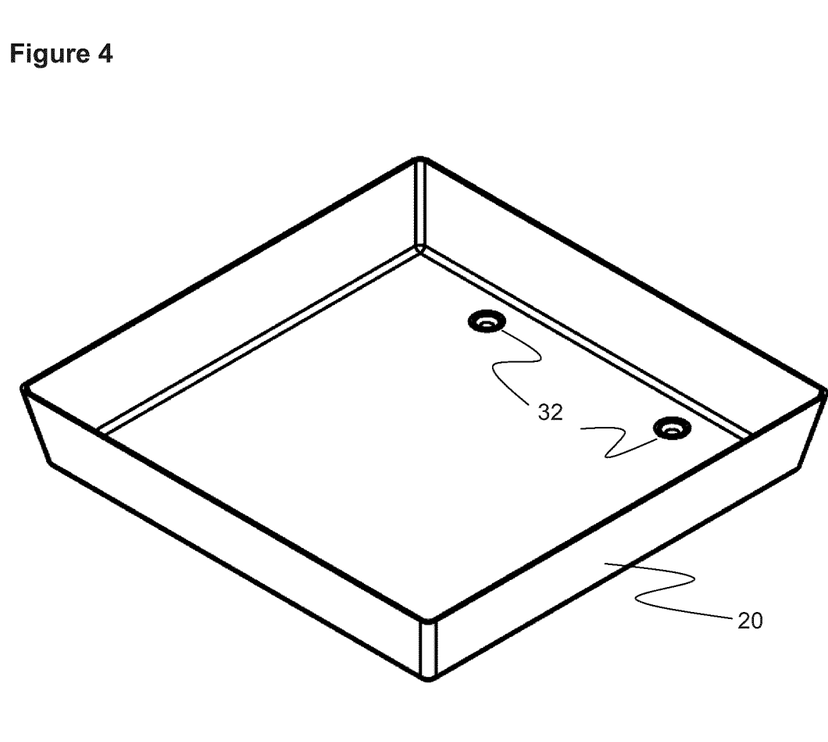
FIG. 4 is an isometric view of a prepupae tray embodiment of a prepupae chamber.
Figure 5:
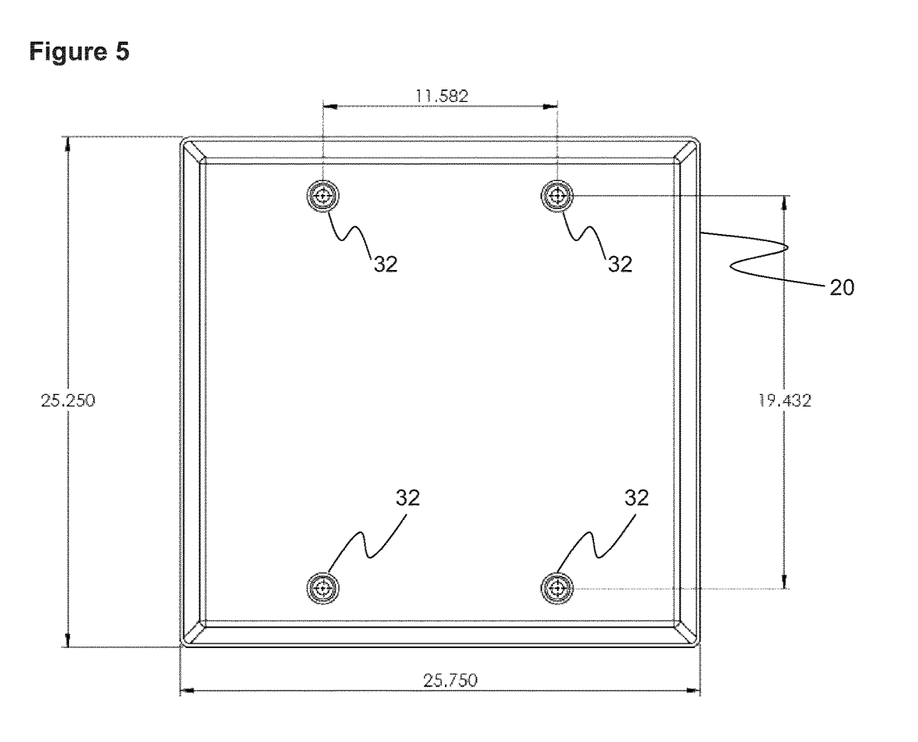
FIG. 5 is a top plan view of the prepupae tray embodiment.
Figure 6:
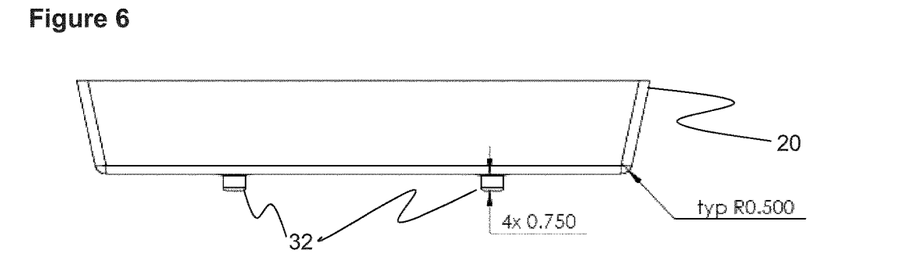
FIG. 6 is an side elevation view of the prepupae tray embodiment.
Figure 7:
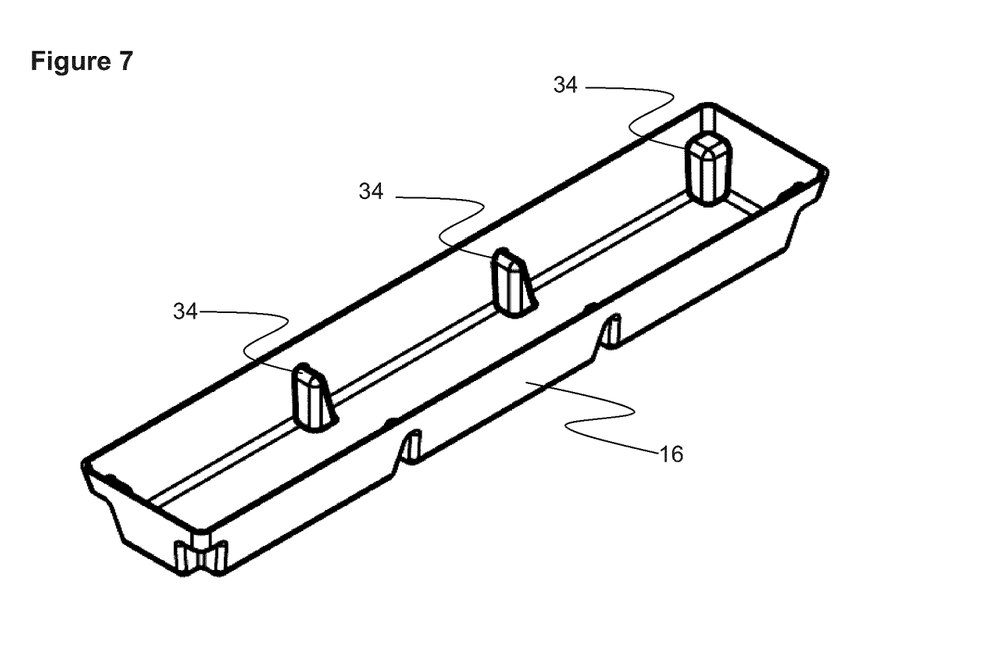
FIG. 7 is an isometric view of an egg tray embodiment of an oviposition chamber.
Figure 8:
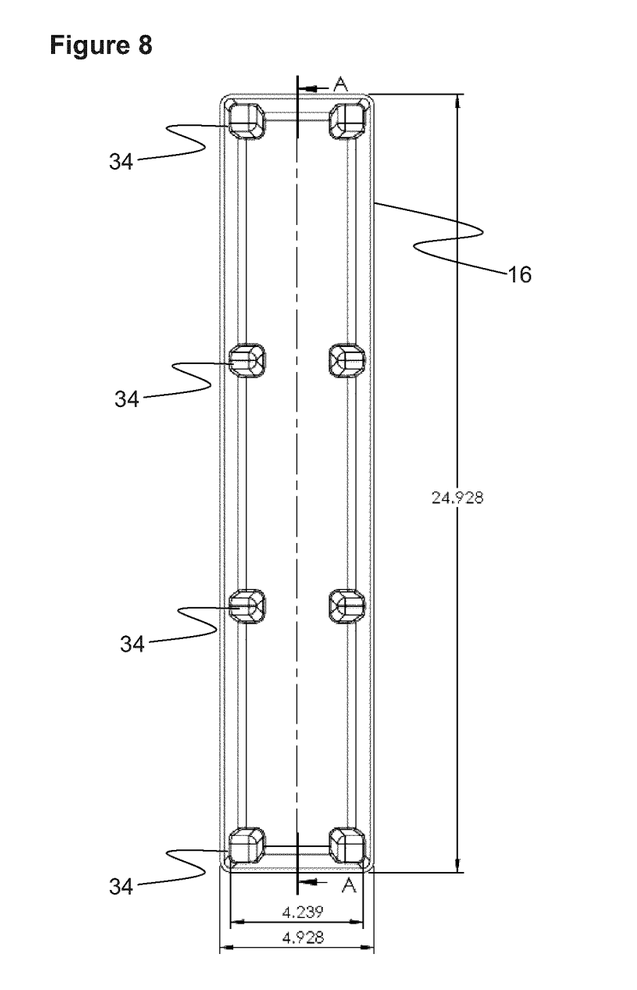
FIG. 8 is a top plan view of the egg tray embodiment.
Figure 9:
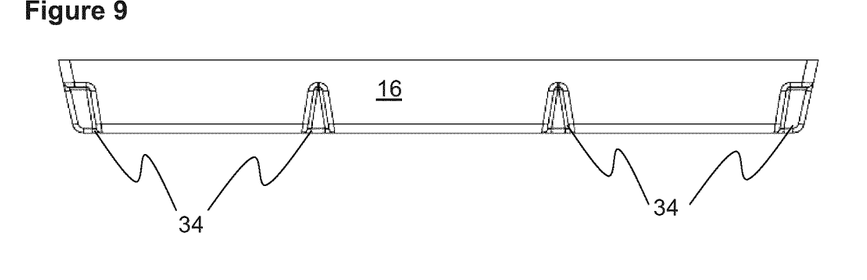
FIG. 9 is sectional side elevation view of the egg tray embodiment, along axis A of FIG. 8.

To facilitate operation of the mating chamber as a conveyor of prepupae and oviposition chambers, the mating chamber may be provided with a prepupae chamber support 22 and an oviposition chamber support 18, each of which act as FIFO accumulating conveyors. For example, prepupae chambers 20 may ride on a support 22 made up of rails, rollers, a belt, or a surface with reduced friction. Alternatively, prepupae and ovipositioning supports may be formed of a continuous or sectioned conveyor belt that runs from a port at one end of mating chamber 10 to a corresponding port at the other end of mating chamber 10. Tabs 32 on the bottom of prepupae chamber 20 may be spaced apart less than the width of the rails 22 in order to guide prepupue chambers 20 in a straight line. For example, tabs 32 can consist of pegs that are glued or attached to the tray or form part of the tray mold. As with other aspects of the mating chamber interior, the surface area of the peg may be minimized to reduce right angles that could act as egg laying areas for gravid females. Prepupae chambers 20 may for example be pushed manually by an operator, or fed mechanically, through an entry port at one end of the mating chamber, which biases against a row of sequential adjoining prepupae chambers 20 riding on support 22, thus displacing the oldest, most distant prepupae chamber 20 out an exit port at the other end of mating enclosure 10. Entry and exit ports 36 are provided for prepupae chambers 20 at the ends of mating chamber 10, as illustrated in FIG. 2. The addition of a new prepupae chamber 20 thereby causes the removal of a spent prepupae chamber 20 at the other end, in which pupae have completed their eclosion. The spent prepupae chamber 20 may be removed from the opposite end of the cage manually or automatically. In a exemplary embodiment, a single prepupae chamber 20 is introduced to the mating chamber daily, so that prepupae chambers 20 are moved one position per day as the sequential chain of prepupae chambers 20 transverses the length of the mating chamber 10. In selected embodiments, the system may be adapted so that a prepupae chamber 20 is resident in the mating chamber 10 for approximately 20 to 30 days, and in any event for a metered prepupae maturation time period that is sufficient for prepupae to metamorphose and eclose as adults.

In the illustrated embodiment, ovipositing chamber 16 consists of a rectangular tray with risers 34 that suspend an ovipositioning substrate (such as a honeycomb structure) above an odoriferous attractant that resides in the bottom of the tray. The ovipositioning chamber 16 advantageously consists of smooth and rounded surfaces, avoiding sharp corners and crevices in order to discourage egg laying on the tray. Ovipositioning chambers 16 cycle through the mating enclosure 10 in a similar fashion to the prepupae chambers 20. In some embodiments, the ovipositioning chamber 16 will be lighter than prepupae chambers 20, so that the ovipositioning chamber support 18 may not require rollers. In the illustrated embodiment, ovipositioning chamber 16 rides on support bars 18 and is manually pushed or pulled by the operator into or out of entry and exit ports 34, as shown in FIG. 2. In this way, the addition of a new ovipositioning tray 16 through port 34 allows for the removal of an ovipositioning tray 16 at the other end of mating chamber 10, through opposing port 34. The sequential ovipositioning chambers 16 riding on support 18 may for example be connected with a hook, magnet or other connector device, and in this way a train of ovipositioning chambers 16 may alternatively be pulled from one end of mating chamber 10 through port 34.

Ovipositioning chambers 16 may be provided with an ovipositioning attractant, for example a saturated 1:1 mixture of Gainesville diet (Hogsette, 1985) mixed with BSF larvae leachate and BSF castings or a mixture of brewery grains and/or wheat bran. Other attractants can include fermenting grain, such as corn brewery grain, manure, decomposing food waste, BSF larvae and/or eggs, fatty acids such as lauric acid. The ovipositioning attractant is formulated and positioned so that it will attract gravid female BSFs to lay eggs on an ovipositioning substrate (such as a honeycomb structure) supported in the ovipositioning chamber 16. In a selected embodiment, a honeycomb ovipositioning substrate consists of material with multiple tubular openings that are open at opposing ends, with openings that may be for example 2-3 mm in diameter and of a variety of shapes.

In alternative embodiments, ovipositioning attractant, such as honeycomb, may for example be suspended above the ovipositioning attractant tray on its own support. In embodiments of this kind, the attractant may for example be provided in a tray or on a continuous belt with sides. The attractant may be fed in one end of the mating chamber 10 and out the other end, through ovipositioning attractant ports. In embodiments of this kind, the ovipositioning substrate may be cycled through mating chamber 10 during a metered period of time, for example 1-2 weeks, before being removed. In systems of this kind, larvae continuously hatch into the attractant, which then acts as a neonate starter feed and is collected and replaced with new feed regularly, for example every 24 hours. In this way, eggs and hatched eggs act as an attractant for gravid females and similarly aged larvae are collected in each batch of neonate substrate.

In selected embodiments, prepupae chambers 20 and ovipositioning chambers 16 may be separated by spacers (eg. ½ inch diameter, ¼ inch high peg) such that chambers are separated by a gap, such as a gap of ¼ inch or more, to discourage gravid females from laying eggs in the cracks between chambers. The spacers may for example be formed as a unitary part of the chambers 16, 20 or may be provided as detachable spacers. Advantageously, trays 16, 20 are smooth with rounded surfaces (having no right angles) in order to discourage egg laying on the tray.

In selected embodiments, ovipositioning trays 16 and prepupae trays 20 are accessed through ports 34, 36, in an arrangement wherein each port is provided with two alternative doors. The alternative doors may for example be constructed to open on opposite sides of the relevant port (top/bottom or left/right). In this system, a primary door is solid, and fully closes the port opening. A secondary door defines an inner opening of smaller dimensions than the port opening, with a deformable inner edge on the inner door opening having dimensions slightly smaller than the transverse cross-sectional dimensions of the ovipositioning or prepupae chambers. During servicing of the ovipositioning or prepupae chambers, the primary door is opened and the secondary door is closed, the secondary door providing access to the chambers through the smaller inner opening therein. When mating chamber 10 is not being serviced, the primary door is closed and the secondary door is open. The inner edges of the secondary door form a deformable opening on the door, for example consisting of bristles and or weather stripping material. As ovipositing or prepupae chambers are pulled or pushed into or out of mating chamber 10, flies are swept off the chambers and substrate by the material of the deformable inner opening, so that adult insects do not escape from mating chamber 10. The primary door allows complete closure of the port opening, while the secondary door allows for flies to be swept off of the chambers as each chamber exits a mating chamber port 34, 36. A two-door system also allows the inner side of each door to be cleaned without flies escaping.

In alternative embodiments, adult insects in mating chamber 10 may be watered using a dedicated watering system. In one embodiment, a radiator line (tube and attached surface area, such as a metal plate) may run the length of the inside of mating chamber 10. A cold fluid, such as water, runs through the radiator line with the temperature of the fluid in the line being below the dew point of the environment (humid air) inside mating chamber 10. In this system, condensation occurs on the metal plates, and flies can drink from this condensate. The fluid temperature may be controlled to prevent excessive dripping from the metal plate. The surface of the metal may be white, to reflect light which attracts flies to the drinking surface. The surface may also be angled away from horizontal, for example at up to 45 degrees, to prevent dead flies from gathering on the surface. In alternative embodiments, low pressure misters may be placed inside or outside the mating chamber 10, such that water droplets accumulate on the sides of the mating chamber mesh or screen, which then acts as a drinking surface for adult flies.

In selected embodiments, adult insects may be provided with a food source, such as a solid sugar substrate, for example a granular or powdered form of solid sugar. It has unexpectedly been discovered that this is effective to increase egg production and longevity of BSFs. The same system that is used as a prepupae chamber system can be adapted for use as an adult insect feed holding and delivery system, including a feeding chamber that moves through the mating chamber along the prepupae chamber support. For example, every $5^{th}$ prepupae chamber may be designated as a feeding chamber. In select embodiments, rice or an alternative type of absorbent may be added to the solid sugar in the feeding chamber to prevent crusting. As the feeding chamber transverses the length of mating chamber 10, for example over a period of 20-30 days, the sugar is consumed by adult flies. An access point, such as a zippered opening in a mesh side, may be inserted at one or more locations along the length of the mating chamber 10, to replenish the feeding chamber with sugar. Although it is widely suggested that adult BSF flies do not consume solid food, adults have been observed in accordance with aspects of the present invention consuming meaningful amounts, for example up to 40 mg, of dry granular sugar over the life of the adult fly. Dry solid sugar generally does not act as an attractant for egg laying females, as females prefer to lay eggs near moister substrates. The feeding chamber may be stocked with additional or alternative sources of nutrition, such as protein, minerals, vitamins or probiotics.

Once eggs are provided by the mating chamber systems, the process of hatching eggs and growing larvae occurs in the bioconversion system. In select embodiments, this bioconversion system consists of stacked trays, which may be of similar or different in size and material. For example, trays may consist of a bottom, 4 sides, and be of at least approximately 5 inches in depth. Trays may be stocked and used interchangeably for a series of segregated tasks: incubation of larvae, grow-out of larvae, or grow-out of prepupae.

In an exemplary bioconversion system, FILO (first in, last out) stacks consist of stacked trays, held by vertical supports with a gap (for example of at least about 5 inches) between trays, to allow for air exchange. Stacks are positioned next to each other with shared supporting posts so that there are no aisles between stacks. A crane suspended from the ceiling or straddling the FILO stacks on rails is positionable to position and transport individual trays to a feed station (where the grow-out trays are fed) or a transfer station in which they are moved out of the stacked system on rollers onto a work station. Multiple cranes can be used to service a single bioconversion unit system (for example 1 crane per row of FILO stacks). A single FILO stack may advantageously remain empty, so that all trays can be cycled through the feeding station.

Once trays reach a work station, they can be moved automatically or manually on rollers to other work stations for servicing (ie. adding/removing egg laying substrate or incubation feeding I or II). An additional crane can be used to transport the tray to a harvesting station. The harvesting station may include a hopper located below the crane/tray. The crane may be positionable to empty the contents by rotating its attachments on the longitudinal axis of the tray, so that the tray is turned upside down and all contents are removed. Alternatively, the crane may set the tray in a tipper unit that is physically independent of the crane. Contents in the hopper can then be transported to a separation station via a belt conveyor or vacuum system.

At the separation station, larvae and larvae frass (dried digestate and other material) can be separated, for example with the use of a zig-zag air separator and/or sieve/screener. Larvae and frass may then be processed separately. For example, frass may be dried and heat treated, larvae may be washed, cooked, dried, cooled or defatted.

In order to maximize hatching success, egg laying substrate may be suspended above a source of neonate feed and incubated in a humid (such as >90% RH) and warm (30-35 C) environment. An example of a food source for newly hatched larvae (neonates) consists of a saturated mixture of approximately 90% brewery grain and 10% wheat bran. In select embodiments, it has been discovered that the mixture of brewery grains and wheat bran can increase the growth rate of larvae by 3-4 times compared to either ingredient on its own. A preservative, such as 0.3% sorbic acid or potassium sorbate may be mixed with the neonate feed to prevent the growth of fungus during the first 4 days of incubation (Incubation I).

During a second phase of neonate incubation (Incubation II), egg laying substrate is removed from the trays and a second feeding is provided. To maximize production and consistency of larval growth, specific larval growth parameters may be adopted in sequential stages of the bioconversion unit, such as metering the number of larvae per unit space (surface area and volume), adjusting feeding frequency and maintaining feed quantity. A target number of larvae per unit space may be optimal in alternative life-cycle stages (L3, L4, L5). In select embodiments, following a selected incubation period, such as approximately 8 days, one or multiple batches of larvae (in incubation trays) are transferred into a mixing device (such as ribbon mixer or drum mixer). As the device mixes the contents, or immediately after mixing, a subsample of larvae/feed mix is extracted from the larvae/feed mix. An estimate of the number of larvae is determined, for example using a minimum of 3 subsamples (# of larvae=# of larvae in the larvae:feed mix/weight of larvae:feed mix×weight of total larvae:feed mix). A grow-out tray is then placed underneath the mixing device onto a load-cell. New feed is added to the grow-out tray. The appropriate amount of larvae:feed mix can then be deposited on top of the new feed in the grow-out tray until the target weight/number of larvae is reached. During larval grow-out in the bioconversion unit, each tray may be fed daily or on alternating days.

In select embodiments, an HVAC system may be deployed around the stacks of the bioconversion unit. In this system, temperature controlled air is pushed and pulled through the stacked system to aid in the removal of carbon dioxide, ammonia, H2O and other metabolic by-products.

Although various embodiments of the invention are disclosed herein, many adaptations and modifications may be made within the scope of the invention in accordance with the common general knowledge of those skilled in this art. Such modifications include the substitution of known equivalents for any aspect of the invention in order to achieve the same result in substantially the same way. Numeric ranges are inclusive of the numbers defining the range. The word "comprising" is used herein as an open-ended term, substantially equivalent to the phrase "including, but not limited to", and the word "comprises" has a corresponding meaning. As used herein, the singular forms "a", "an" and "the" include plural referents unless the context clearly dictates otherwise. Thus, for example, reference to "a thing" includes more than one such thing. Citation of references herein is not an admission that such references are prior art to the present invention. Any priority document(s) and all publications, including but not limited to patents and patent applications, cited in this specification are incorporated herein by reference as if each individual publication were specifically and individually indicated to be incorporated by reference herein and as though fully set forth herein. The invention includes all embodiments and variations substantially as hereinbefore described and with reference to the examples and drawings.

The invention claimed is:

1. A continuous system for culturing dipteran insects, comprising:
   a mating chamber and a bioconversion unit, wherein the mating chamber is adapted to house male and female adult insects that mate to produce insect eggs that are transferred from the mating chamber to the bioconversion unit for rearing, and the bioconversion unit is adapted to rear insect larvae to produce matured larvae that are transferred to the mating chamber to eclose to produce adult insects;
   the mating chamber comprising:
   an enclosure for containing the adult insects, adapted to permit air circulation into and out of the enclosure and to admit external illumination into the enclosure, the enclosure having an entry port and an exit port for an oviposition chamber, and an entry port and an exit port for a prepupae chamber;
   an oviposition chamber support housed within the enclosure, adapted to convey an egg laying substrate in the oviposition chamber from the oviposition chamber entry port to the oviposition chamber exit port;
   a prepupae chamber support housed within the enclosure, adapted to convey the prepupae chamber from the prepupae chamber entry port to the prepupae chamber exit port;
   a mort collection system disposed along the base of the mating chamber, adapted to convey dead insects out of the mating chamber through a mort exit port in the enclosure; and,
   a mechanism for sequentially passing oviposition chambers through the enclosure along the oviposition chamber support during a metered ovipositioning period;
   a mechanism for sequentially passing prepupae chambers through the screened enclosure along the prepupae chamber support during a metered prepupae maturation period, wherein the prepupae maturation period is longer than the ovipositioning period;
   the bioconversion unit comprising:
   a plurality of segregated larval compartments each adapted to house insect larvae and growth media; and,
   a mechanism for sequentially feeding metered growth media to the larvae in a selected larval compartment;
      wherein eggs produced in the mating chamber on the egg-laying substrate are seeded in a neonate larval compartment of the bioconversion unit by transferring the egg-laying substrate to the neonate larval compartment and providing a neonate food source in the neonate larval compartment accessible to neonate insect larvae, wherein an approximated collection of eggs or hatched neonates are seeded in the neonate compartment and allowed to mature on the neonate food source to produce matured neonate larvae;
      wherein barren egg-laying substrates are sequentially separated from matured neonate larvae and neonate larval compartments, and returned to oviposition chambers in the mating chamber, and matured neonate larvae are then sequentially fed with metered growth media in larval compartments of the bioconversion unit, to produce matured larvae, and metered populations of matured larvae are then sequentially transferred to the prepupae chambers in the mating chamber to eclose to produce the adult insects.

2. The system of claim 1, wherein the mating chamber and bioconversion unit are housed in a climate-controlled enclosure.

3. The system of claim 2, wherein the climate controlled enclosure admits sunlight and/or artificial light, and the mating chamber is positioned within the climate-controlled enclosure so that sunlight reaches the adult insects within the mating chamber.

4. The system of claim 1, wherein matured larvae are segregated and harvested from the bioconversion unit to produce a feed.

5. The system of claim 4, wherein the feed comprises separate meal fractions having distinct protein and lipid components.

6. The system of claim 1, wherein frass produced by maturing larvae in the bioconversion unit is segregated and harvested from the bioconversion unit.

7. The system of claim 1, wherein the mating chamber comprises a feeding mechanism for introducing adult fly food into the chamber.

8. The system of claim 7, wherein the feeding mechanism comprises adult feed containers adapted to travel along the oviposition chamber support or the prepupae chamber support.

9. The system of claim 8, wherein the adult fly food comprises solid sugar.

10. The system of claim 1, further comprising a light source positioned to illuminate the enclosure, wherein the prepupae chambers are positioned between the light source and the ovipositioning chambers in the mating chamber, so that the prepupae chambers shade the ovipositioning chambers from the light source.

11. The system of claim 1, wherein the neonate food source comprises a combination of brewery grains and wheat bran.

12. The system of claim 11, wherein the neonate food source comprises from 80% to 95% brewery grains and from 5% to 20% wheat bran.

13. The system of claim 1, wherein the dipteran insects comprise *Hermetia illucens*.

14. The system of claim 1, wherein the bioconversion unit further comprises a first in, last out, system of stacked larval compartments.

15. The system of claim 14, wherein the bioconversion unit further comprises one or more cranes positionable to position and transport larval compartments.

16. A mating chamber for culturing dipteran insects, comprising:

an enclosure for containing adult insects, adapted to permit air circulation into and out of the enclosure and to admit external illumination into the enclosure, the enclosure having an entry port and an exit port for an oviposition chamber, and an entry port and an exit port for a prepupae chamber;

an oviposition chamber support housed within the enclosure, adapted to convey an egg laying substrate in the oviposition chamber from the oviposition chamber entry port to the oviposition chamber exit port;

a prepupae chamber support housed within the enclosure, adapted to convey the prepupae chamber from the prepupae chamber entry port to the prepupae chamber exit port;

a mort collection system disposed along the base of the mating chamber, adapted to convey dead insects out of the mating chamber through a mort exit port in the enclosure; and, a mechanism for sequentially passing oviposition chambers through the enclosure along the oviposition chamber support during a metered ovipositioning period;

a mechanism for sequentially passing prepupae chambers through the screened enclosure along the prepupae chamber support during a metered prepupae maturation period, wherein the prepupae maturation period is longer than the ovipositioning period.

* * * * *